United States Patent [19]
Chesebro et al.

[11] Patent Number: 5,811,282
[45] Date of Patent: Sep. 22, 1998

[54] CELL LINES USEFUL FOR DETECTION OF HUMAN IMMUNODEFICIENCY VIRUS

[75] Inventors: Bruce Chesebro, Corvallis; Kathy Wehrly, Hamilton, both of Mont.

[73] Assignee: The Unites States of America as represented by the Secretary of the Department of Health and Human Services, Washington, D.C.

[21] Appl. No.: 480,365

[22] Filed: Jun. 7, 1995

Related U.S. Application Data

[63] Continuation of Ser. No. 478,081, Feb. 9, 1990, abandoned, which is a continuation-in-part of Ser. No. 168,493, Mar. 15, 1988, abandoned.

[51] Int. Cl.$^6$ ................................................. C12N 5/10
[52] U.S. Cl. ................... 435/240.23; 435/240.1; 435/240.21; 435/974
[58] Field of Search .................. 435/5, 7.1, 7.2, 435/3.24, 240.1, 240.21, 240.23, 245, 974

[56] References Cited

PUBLICATIONS

Maddon et al: The T4 Gene Encodes the AIDS Virus Receptor and is Expressed in the Immune System and the Brain, Cell, v.47, pp. 333–348 Nov. 7, 1986.

Stanley. "Membrane Mutants of Animal Cells Rapid Identification of Those with a Primary Defect in Glycosytation" Molecular & Cell. Biol. V5, #5 May 85 pp. 923–929.

Catalogue of ATCC Cell lines & Hybridomas, 5$^{th}$ ed. 1985 pp. 3–5, American Type Culture Collectioin, Rockville, MD.

Chesebro, B., et al., "Failure of Human Immunodeficiency Virus Entry and Infection in CD4–Positive Human Brain and Skin Cells." J. Virology 64:215–221 (1990).

Maddon, et al., "The T4 Genes Encodes the AIDS Virus Receptor and is Expressed in the Immune System and the Brain" Cell 47:333–348 (1986).

Stanley, P. "Membrane Mutants of Animal Cells: Rapid Identification of Those with a Primary Defect in Glycosylation." Mol. & Cell Biol. 5:923–929 (1985.

Catalogue of ATCC Cell Lines & Hybridomas, 5th Ed., 1985, pp. 3–5. American Type Culture Collection, Rockville, MD.

Maddon et al. "The T4 Gene Encodes the AIDS Virus Receptor and Is Expressed in the Immune System and the Brain." *Cell*, vol. 47, Nov. 7, 1986, pp. 333–348. QH573.C38.

Stanley. "Membrane Mutants of Animal Cells: Rapid Identification of Those with a Primary Defect in Glycosylation." *Molecular and Cellular Biology*, vol. 5, No. 5, May 1985, pp. 923–929. QH506 .M6.

Catalogue of ATCC Cell Lines & Hybridomas, 5$^{th}$ edition, 1985, pp. 3–5, American Type Culture Collection, 12301 Parklawn Drive, Rockville, MD 20852–1776, Library of Congress Catalog Card No. 85–71973.

*Primary Examiner*—Christine M. Nucker
*Assistant Examiner*—Jeffrey Stucker
*Attorney, Agent, or Firm*—NIH Office of Technology Transfer

[57] ABSTRACT

The present invention relates to a method for AIDS diagnosis and monitoring of anti-AIDS drug therapy, and more particularly to a method of assaying for human immunodeficiency virus. The present invention uses a focal immunoassay (FIA) which utilizes HIV-specific antibodies and indirect immunoassay techniques to detect local areas of HIV infection in susceptible target cells growing in monolayers on plastic dishes. The present invention further relates to specific cell lines used as the susceptible target cells in the disclosed methods.

8 Claims, 4 Drawing Sheets

CELL LINES USEFUL FOR DETECTION OF HUMAN IMMUNODEFICIENCY VIRUS

This application is a continuation of application Ser. No. 07/478,081, filed Feb. 9, 1990, now abandoned, which is a continuation-in-part of application Ser. No. 07/168,493, filed Mar. 15, 1988, abandoned.

The present invention relates to a method for AIDS diagnosis and monitoring of anti-AIDS drug therapy, and more particularly to a method of assaying for human immunodeficiency virus.

BACKGROUND OF THE INVENTION

AIDS is a relatively newly recognized disease. To date, thousands of cases have been reported, and the disease has elicited great concern because of the rapid expansion of the epidemic and the high mortality rate of the disease. Its overwhelming prevalence among homosexual men with multiple sexual partners, users of illegal intravenous drugs, hemophiliacs, blood transfusion recipients, and close heterosexual contacts of members of the above high-risk groups strongly suggests that the disease spreads by the transmission of an infectious agent. The primary targets of affliction in the human body are specific subpopulations of T-cells. The severe immune deficiency of patients with AIDS results from an unusually low proportion of helper T-cells (T4 cells) in their lymphocyte population, thus reducing the availability of many T4 helper functions, among which is the production of antibodies by B-cells.

Retrovirus infection is known to lead to depressed immune function in animal systems. Analogizing the human response to these non-animal systems, a human retrovirus with a tropism for T-cells was considered a candidate in the etiology of human AIDS.

Several members of a family of human T-lymphotropic retroviruses (HTLV) have been isolated. One of these isolates was obtained from a patient with an aggressive form of T-cell lymphoma. This virus, designated as HTLV-I, has been etiologically linked to the pathogenesis adult T-cell leukemia/lymphoma (ATLL). In vitro infection with HTLV-I can alter T-cell function and, in some cases, lead to T-cell death. Another member of the HTLV family was isolated from a patient with a T-cell variant of hairy cell leukemia, and was designated HTLV-II. Isolation of the HTLV-I and HTLV-II have been reported from cultured T-cells of patients with AIDS. Isolation of another retrovirus was reported from a homosexual patient with chronic generalized lymphadenopathy, a syndrome that often precedes AIDS and therefore is referred to as "pre-AIDS". Proviral DNA of HTLV-I was detected in the cellular DNA of two AIDS patients, and sera of some patients were shown to react with antigens of HTLV-I. The correlation between AIDS and serum antibodies to HTLV-I protein is weak.

It has now been shown that the primary cause of AIDS is a human T-lymphocytic retrovirus variant with limited cross-reactivities with the known HTLV subgroups. These new variants are designated HTLV-III, or, more recently, HIV.

Since AIDS and human immunodeficiency virus (HIV) are known to be transmitted by blood products, a method for detecting contamination of blood by HIV is needed to guarantee the safety of recipients of blood. Such a test method should be as sensitive and specific as possible, and should also be easily performed in a routine environment. Tests for viral markers such as reverse transcriptase, viral antigens, or nucleic acid sequences in fresh or cultured blood cells are slow and are presently not suitable for large-scale screening. On the other hand, serological tests for viral antibodies or antigens are well suited for this purpose, since HIV infected individuals are generally seropositive for antibodies to one or more HIV proteins.

Quantitative measurement of HIV, the agent of acquired immune deficiency syndrome, is currently a technically difficult procedure. Primary isolation of HIV from patients is usually done in PHA- or allogenically-stimulated human lymphocyte blast cell cultures. This procedure was subsequently adapted using end-point dilution to give a quantitative (ID50) estimate of infectious virus. However, for many studies, an enumeration, or "plaque", assay would be highly desirable.

A plaque test has been described in HTLV-I-carrying cell lines by Harada et al., in *J. Clin. Microbiol.* 25, 1305 (1987). This assay is quantitative and useful for the LAV/HTLV IIIB strain of HIV, but it is less sensitive than the use of normal human lymphocyte blast cultures and does not work on wild-type HIV isolates. Furthermore, viruses recovered from such cells have the potential to be altered by recombination with HTLV-I-derived gene sequences, thus obscuring the true genetic structure of the original input HIV strain.

Previous work with other retroviruses has indicated that assay of virus-infected cells by infectious center assay on susceptible monolayers of cells adherent to plastic dishes is a highly sensitive quantitative detection method. Furthermore, focal areas of virus infection can be identified using virus-specific monoclonal or polyclonal antibodies, thus eliminating the requirement for a focal cytopathic effect at each site of infection, which can be difficult or impossible to obtain in certain virus-cell combination. Finally, if detection is done in living cells, biologically cloned viruses can be directly obtained from heterogeneous populations. Such an approach has not been possible with HIV because of the lack of suitable plastic-adherent target cells.

Gallo et al., in U.S. Pat. No. 4,520,113, disclose a method for detecting antibodies to AIDS in sera by either a strip radioimmunoassay based on the Western Blot technique, or ELISA, an enzyme-linked immunosorbent assay.

Currently the standard test for the presence of live HIV in human blood, tissue, or fluid samples involves incubation of samples to be tested together with activated T-lymphocytes obtained from normal human blood. Subsequently, these T-lymphocytes are cultured continuously for up to five weeks, and the culture fluid is examined periodically for the presence of reverse transcriptase enzyme found within HIV virus particles. This culture isolation procedure is not quantitative, and its sensitivity is unclear.

Focal immuno assay (FIA) is a known assay technique, but it has not been used to assay for HIV-infected cells or HIV in the absence of cells because of the lack of appropriate target cells, specific anti-HIV antibodies, and the requisite procedural details to make the test work for HIV.

Most cell lines used for laboratory HIV infection studies grow as suspension cultures in liquid medium, In this case, rare infected cells float around in the cultures, spreading infection randomly. This can only be detected when the level of infected cells has spread enough to be detected by immunofluorescence or reverse transcriptase analysis. This usually takes from about two to four weeks for low levels of initial infection.

SUMMARY OF THE INVENTION

It is an object of the present invention to overcome deficiencies in the prior art, such as those noted above.

It is another object of the present invention to assay for HIV-infected cells.

It is a further object of the present invention to test for cell-free HIV.

It is still another object of the present invention to provide an improved, more accurate, simplified and faster test for diagnosing AIDS.

It is yet another object of the present invention to monitor levels of HIV or HIV-infected cells in samples obtained from humans.

It is yet a further object of the present invention to monitor levels of HIV or HIV-infected cells in samples produced in laboratory situations.

It is yet another object of the present invention to provide a method for preparing an anti-HIV monoclonal antibody.

It is still a further object of the present invention to select a susceptible target cell for use in an assay for HIV.

The assay according to the present invention is a focal immuno assay (FIA) which uses HIV-specific antibodies and indirect immunological assays such as immunocytochemistry or autoradiography immunofluorescence, to detect local areas, or foci, of HIV infection in susceptible target cells growing in monolayers.

The test according to the present invention is both quantitative and highly sensitive. On laboratory HIV strains a single HIV-infected cell can be detected in a sample containing one million uninfected cells, and higher percentages of infected cells can be accurately quantitated. This procedure allows monitoring of the effects of drug therapy on levels of HIV expression in AIDS patients, as well as providing a quantitative measure of HIV expression in asymptomatic HIV antibody-positive individuals. The test according to the present invention is rapid, requiring only two to four days to complete, which is a major advantage compared to presently available tests.

The test according to the present invention is more sensitive for HIV-infected cells than for cell-free HIV. Nevertheless, the test does work with cell-free virus, and can be used to measure virus neutralizing antibody more quantitatively, since individual foci of virus infection can be counted.

To test the efficiency of the present invention, various dilutions of HIV or HIV-infected cells were placed into dishes previously seeded with cells susceptible to HIV infection. After incubation, the cells were exposed to antibody reactive with HIV proteins or a monoclonal antibody for the gp 120 envelope protein of the LAV/HTLV IIIB strain of HIV, exposed to marker-conjugated antibody reactive with the first antibody used, and incubated. After short term culturing, the dishes were then examined by appropriate means such as a fluorescent microscope or a light-microscope, and the number of foci of immunofluorescent-positive cells per dish were counted.

A process according to the present invention to test for the presence and/or extent of HIV infection involves the steps set forth above, except for addition of HIV or HIV- infected cells.

To insert the appropriate target cells, HeLa cells were infected with a retroviral vector containing the CD4 gene and neomycin resistant gene. After infection, the cells were grown in the presence of the neomycin analog, G418, and resistant clones were selected. Of eighteen clones analyzed, four were found to express cell surface CD4 detectable by membrane immunofluorescence using the monoclonal antibody OKT$_Y$, and one clone, HT4-60, was used in subsequent studies.

DETAILED DESCRIPTION OF THE INVENTION

The present invention uses a focal immunoassay (FIA) which uses HIV-specific antibodies and indirect immunoassay techniques to detect local areas or HIV infection in susceptible target cells growing in monolayers on plastic dishes.

Varying dilutions of the sample to be tested, whether unknown or known to contain HIV or HIV-infected cells, are placed into dishes seeded one day previously with cells susceptible to HIV infection. Any suitable growth medium may be used, such as those selected from known growth media. Selection of cells susceptible to HIV infection is important, although not limited to any single type of cells. However, the susceptible target cell must be one which will grow attached to the testing dishes, Preferably formed of plastic. Suitable target cells are mentioned in the examples below.

Two to four days later growth medium is removed, and cells are fixed, for example by methanol or other suitable fixers such as four or five to ten minutes. After rinsing of the fixation cells, e.g. with conventional aqueous buffer, the rinsed fixation cells are exposed to an appropriate dilution and volume of antibody reactive with HIV proteins. Again, the selection of anti-HIV antibody is an important consideration, and it is necessary to select the anti-HIV antibody from among those which are capable of detecting some HIV strains in fixed or live infected cells with a high degree of sensitivity. Suitable materials are mentioned in the examples.

After exposure, for thirty minutes, it is desirable to again wash with an aqueous buffer. The so-treated cells are then exposed to marker-conjugated antibody reactive with the first antibody. The marker-conjugated antibody may be conjugated with any suitable marker material such as fluorescene isothiocyanate (FITC) which may be purchased from commercial sources, although clearly other materials can be used. Optimally, a supplemental protein such as bovine serum albumin (BSA) or fetal calf serum (FCS) can be used to enhance responsiveness of the cells.

After further incubation, e.g. thirty minutes, the dishes are again washed, e.g. twice with aqueous buffer. Next, the cells are either fixed, e.g. with methanol or 2% formalin or reacted with suitable chemicals to visualize conjugated antibodies. After optional further washing and removal of fluid, the dishes are subjected to examination in a fluorescence or light microscope or autoradiograph, depending upon the type of marker used.

It was necessary to develop a susceptible target cell for use in the assay of the present invention. A susceptible target cell was developed which would grow attached to plastic dishes. In order to accomplish this, the CD4 gene encoding the HIV receptor molecule, T4, was transferred to a human carcinoma cell line, HeLa. Eighteen different T4- positive HeLa cell clones were derived and screened for HIV infection. Many were negative, and among the positive clones different levels of HIV infectibility were seen. The best clones were chosen for further experiments.

Infection was carried out by placing various dilutions of HIV or HIV-infected cells into dishes which had been seeded one day previously with cells which are susceptible to HIV infection. Two to four days after infection, the growth medium was removed, and the cells were fixed by exposure to methanol for from about five to about ten minutes. After fixation, the cells were rinsed twice with aqueous buffer, exposed for about thirty minutes to an appropriate dilution and volume of mouse or human antibody reactive with HIV proteins, washed once with aqueous buffer, and exposed to a marker-conjugated antibody reactive with the first antibody used.

The anti-HIV antibody was selected as follows. Initially, several mouse monoclonal antibodies specific for the HIV envelope protein were generated, gp120, which were capable of detecting some HIV strains in methanol-fixed or live infected cells with high sensitivity. These monoclonal antibodies were used in the initial development of procedural details of the FIA and selection of the best target cell clone. However, because it was feared that these antibodies might not detect wild type HIV strains as well as human AIDS patient serum, human AIDS patient serum was also used for HIV detection in the FIA. Initially, this was a problem, since AIDS patient serum contains many antibodies other than anti-HIV. However, by extensive absorption of serum with uninfected human lymphocytes and HeLA cells, non-specific reactivity could be eliminated and absorbed human AIDS patient sera were effective in the test. This monoclonal reacts with the gp 120 protein but does not block the CP 14. The gp 120's can be tagged without interfering with the other reaction.

Monoclonal antibodies reactive with the envelope protein of HIV were generated, ATCC number CRL 9631. Two different antibodies, designated as 902 and 907, were obtained, which antibodies immunoprecipitated the gp 160 and/or gp 120 envelopes from HIV-infected cells or virions, and were shown to be specific for gp 120 by their reactivity with cells infected with vaccine virus encoding HIV gp 120.

The second step in the detection method according to the present invention uses marker-conjugated antibodies reactive with the human or mouse immunoglobulins used in the first step. These marker-conjugated antibodies can be purchased from commercial sources, such as Cappel Laboratories, in West Chester, Pa.

After another incubation of about thirty minutes, the dishes were washed twice again with buffer and fixed again with methanol in 2% formalin or processed to develop marker-specific staining. After one additional aqueous wash, fluid was removed, and the dishes were examined in a suitable detection means, microscope such as a fluorescence microscope or light microscope of an autoradiograph.

The number of foci of marker-positive cells per dish were then counted. Usually these foci consist of from about 1 to about 30 cells in a small area sometimes containing one or more cells with multiple nuclei (about 2 to more than 30). Since from about one to about five million lymphocytes or monocytes can be placed in a single dish, and one can detect a single focus in a dish, the assay can detect approximately one infected cell per one to five million cells tested.

Other variables which have been dealt with to make the assay of the present invention successful include the density of the target seeding ($5 \times 10^4$ per 35 mm dish), number of days between infection and focus detection (2 to 4 days), type of fixation, and method of observation.

The present inventors have previously found that monoclonal antibodies specific for retroviral envelope proteins were very useful as specific immunological reagents to detect lie or fixed virus-infected cells. To facilitate development of an HIV assay, monoclonal antibodies were generated which were reactive with the envelope protein of HIV. Two different antibodies, designated was 902 and 907, were obtained which immunoprecipitated the gp160 and/or gp120 envelope proteins from HIV-infected cells or virions, and were shown to be specific for gp 120 by their reactivity with cells infected with vaccinia virus encoding HIV gp120.

To perform the assay for HIV-infected cells, monolayer cultures of HT4-6C cells were used to detect A3.01 human T lymphocytes infected in vitro with the LAV strain of HIV. Cells from infected A3.01 cultures were placed into dishes seeded one day previously with HT4-6C cells. The following day, suspended cells were removed, and the medium was changed. Three days later, the foci of infected cells were identified by the focal immunofluorescence assay using monoclonal antibody 902, reactive with HIV envelope protein. Multiple foci of infected HT4-6C cells were seen. Immunoflourescent cells were often multinucleated, but also appeared grouped in clusters of 10–20 mononuclear cells, as shown in FIGS. 2A and 2B. The observation of clusters of HIV infected mononuclear cells suggested that the LAV strain of HIV might be able to spread in HT4-6C cells without cell-to-cell fusion.

A similar assay was effected using three day PHA-stimulated human lymphocytes infected with a patient HIV isolate not previously adapted to growth in in vitro lymphoid cell lines. In this case, foci were detected using a polyclonal human anti-HIV AIDS patient serum, and the foci observed usually consisted of multinucleated giant cells, either alone or in groups of two or three together, as shown in FIG. 2C.

Focal immunofluorescence assay was also successfully carried out using live infected HT4-6C cells without methanol fixation, as seen in FIG. 2D. Under these conditions, foci were less obvious and few, if any, fluorescent multinucleated giant cells were seen. Examination of these cultures with visible light suggested that large syncytial cells were removed from the dishes during the multiple washing steps of the FIA procedure. Remaining fluorescent cells appeared to be mononuclear, and cells from each focus should potentially be a source of biologically cloned live HIV.

Since HIV-infected A3.01 lymphocyte suspension cultures contained both cell-free HIV virions and cell-associated HIV budding from live infected cells, it was of interest to determine which source of HIV was responsible for the foci detected by FIA in HT4-6C cells. FIA analysis of cell suspensions indicated that only 1% of the original foci were detectable after infection with cell-free supernatant fluid, as shown in FIG. 3. Thus, 99% of the foci were due to cell-associated HIV, and these foci were mostly eliminated if the cells in suspension were killed by Dunce homogeniaztion.

In contrast, neither X-irradiation (10,000 rads) nor treatment with trypsin reduced the number of foci detected from the cell suspension. These results suggested that the HIV foci detected in the plastic adherent HT4-6C cells were induced by transfer of HIV from infected lymphoid cells and not from cell-free virus.

To test the sensitivity of the FIA in HT4-6C cells, this assay was compared with indirect immunofluorescence (IF) of HIV-infected A30.01 cells, or PHA blast cells for its ability to detect spread of HIV infection in lymphocyte suspension cultures. The immunofluorescence assay was not capable of scoring infected cells at an incidence below 0.1% because of a background of cells with non-specific fluorescence artifacts. However, the FIA could detect HIV infection at a level as low as 0.0001% cells (3 foci per $3 \times 10^6$ cells seeded in a 35 mm dish).

In a range where the two assays could be compared, there was an excellent correlation between the percent of cells detected in either assay, cf. FIGS. 4A and 4B. Thus, the FIA appeared to detect most or all of the cells expressing viral proteins. However, in older (11 day) PHA blast cell culture, the FIA and the immunofluorescence assays did diverge. At this time, one cultures appeared to accumulate dead or dying HIV-infected lymphocytes which were scored by immunofluorescence but not by FIA.

In these experiments, reverse transcriptase was also measured in the supernatant fluids of the infected A3.01 and PHA blast cell cultures. In both cases the FIA was found to be far more sensitive than the reverse transcriptase. In A3.01 cells RT became positive only after greater than 1% of cells were infected, whereas, in blast cells reverse transcriptase was positive when greater than 0.1% of cells was infected.

In other experiments with different HIV isolates, FIA and immunofluorescence assays were not always in agreement. In all cases, the FIA was more sensitive than either the reverse transcriptase or the immunofluorescence. However, the number of cells scored by FIA ranged from 5 to 100% of the cells scored by immunofluorescence. Also, in certain chronically infected cell lines, such as H9 cells infected with HTLV IIIB (ATCC # CRL8543), only 1–5% of the cells scored positive by FIA. These cells produced very low levels of cell-free infectious HIV.

Initial experiments illustrated in FIG. 3 suggested that the FIA in HT4-6C cells was also capable of detecting infection by cell-free HIV. Furthermore, a dilution titration of HIV on HT4-6C cells gave a one hit kinetic curve, i.e., a two-fold dilution gave a two-fold decrease in foci detected, as shown in FIG. 5. Thus, each focus appeared to represent infection by a single HIV virion.

In order to test the sensitivity of this system, a comparison was made of titration of cell-free virions on HT4-6C, A3.01, and PHA blast cells. The results indicated that A3.01-adapted HIV, LAV strain, was detected with similar efficiency on HT4-6C, A3.01, and PHA blast cells. In the case of wild type HIV isolates not adapted to grow in A3.01 cells, HT4-6C cells detected only 0.1 to 1% of the infectivity observed in PHA blast cell cultures. These same virus isolates were not detected at all in A3.01 cell cultures.

Optimal conditions for detection of cell-free HIV appeared to be different for HIV(LAV) and wild-type HIV isolates. Polybrene and DEAE dextran have frequently been used to increase the efficiency of retrovirus infection in vitro., cf. Toyoshima et al., *Virology* 38, 414 (1969). With HT4-6C cells, infection by HIV (LV) was equally effective with or without DEAE-dextran; surprisingly, polybrene appeared to inhibit infection. In contrast, wild-type HIV isolates were detected only when cells were pretreated with DEAE-dextran; no treatment and infection in the presence of polybrene were not successful.

The cause of the relative inefficiency of initial infection of HT4-6C cells by wild-type HIV virions is unknown. This may be due to an insufficient quantity of T4 receptor molecules expressed on these cells. In this regard, 18 other HeLa clones infected with the CD4 expression vector were tested, and a large variation in sensitivity of HIV detection was found. Alternatively, it is also possible that other receptor molecules besides T4, and even membrane lipid composition, might contribute to more efficient HIV infection.

Because of its high potential sensitivity in detecting HIV-infected cells, the FIA was used to detect HIV infection in lymphocytes obtained from AIDS patients. Patient cells were also co-cultivated with normal PHA blast cells, and culture fluids and cells were assayed for HIV at various times by FIA or by reverse transcriptase, cf. Table 1.

TABLE 1

Use of focal immunofluorescence assay (FIA) and reverse transcriptase (RT) assay to detect HIV infection in AIDS patient lymphocytes co-cultivated with normal lymphocytes.

| Patient | Day 0 | Foci/$10^6$ cells | | | | | | |
|---|---|---|---|---|---|---|---|---|
| | | 4 | 7 | 10 | 14 | 18 | 21 | 24 |
| 6853 | <1 | 1920 | 610 | 140 | 35 | nt | nt | nt |
| 6588 | <1 | 21 | 1400 | 2800 | 700 | 420 | 280 | 1400 |
| 6585 | <1 | 70 | 1050 | 350 | 14 | 7 | 14 | 21 |
| 6435 | <1 | | <20 | 35 | 1400 | 700 | 140 | nt |
| 6598 | <1 | | <20 | 35 | 35 | 20 | <20 | <20 |
| 6597 | <1 | | <20 | 35 | <20 | 35 | <20 | 140 |
| 6428 | <1 | | | <20 | 840 | 560 | 350 | nt |
| 6426 | <1 | | | <20 | 513 | 280 | 280 | nt |
| 6589 | <1 | | | <20 | 70 | <20 | 35 | <20 |
| 6859 | <1 | | | | <20 | 63 | 70 | 175 |
| 6856 | <1 | | | | <20 | 35 | 30 | 23 |
| 6857 | < | | | | | <20 | 35 | <20 |
| 6848 | <1 | | | | | <20 | 35 | <20 |
| 6852 | <1 | | | | | | <20 | 23 |

[1] Threshold for positive by focal immunofluorescence assay (FIA) was greater than 3 foci per 35 mm dish of HT4-6C cells infected 4 days earlier with either $3 \times 10^4$ freshly isolated Ficoll-Hypaque banded peripheral blood mononuclear cells, or in the case of cultured cells, 0.05 to 0.25 ml of lymphocyte culture suspension containing 0.25 to $1.25 \times 10^5$ cells. Positive reverse transcriptase (RT) was greater than 200 cpm $^{3cP}$-dTTP incorporated into DEB1 paper binding material per 3.5 ul culture supernatant fluid in a 30 minute assay as described previously (23). Cultures positive for RT are indicated by underlining of the value shown for the FIA.

[2] Cultures of B patients in these experiments were negative by both FIA and RT at all times tested through 24 days.

[3] nt=not tested; blank values were negative by FIA (<20 foci/$10^6$ cells) and by RT.

[4] Cultures consisted of upright 25 cm$^2$ flasks with 10 ml RPMI 1640 with 10% fetal calf serum, 10 μg PHA/ml, and $5 \times 10$-5M, 2-mercaptoethanol plus 4 to $5 \times 10^6$ Ficoll-Hypaque-banded peripheral blood mononuclear cells from AIDS patients and 4 to $5 \times 10^6$ similar mononuclear cells from normal human blood stimulated in vitro 3 days earlier by culture at $2 \times 10^6$ cells/ml with PHA at 10 μg/ml in medium as above. Cultures were fed every 2 to 3 days with medium containing 5% IL-2-positive culture medium (Electronucleonics, Rocksville, Md.), and every 7 days $4 \times 10^6$ new 3 day PHA stimulated normal human lymphocytes were added.

Analysis of these cultures by FIA was not difficult during the initial 14 to 18 days, however, after this time the cells in these cultures became quite toxic for the HT4-6C cells, and to avoid this effect fewer lymphocytes were added to each HT4-6C well, thus reducing the sensitivity of the FIA.

5. AIDS patients were randomly selected individuals from the NIAID 11th floor AIDS patient clinic at NIH, Bethesda, Md., who were positive for HIV antibodies by both ELISA and Western blot.

A new cell line recently discovered which has been designated as 1022 cell line has now been used in the method of the invention. The cell line is 10× to 330× more sensitive than the HT4-6C cell line at detecting wild-type HIV strains directly after isolation from AIDS patients. The cells of Maddon are compared with the HT4-6C and 1022 cell lines of the present invention. While Maddon suggests many of the aspects of the current method, the cells of Maddon are not reliable for purposes of the invention, since the foci of the HIV infection are difficult to observe due to the roughness of the monolayer and the number of foci detected is very low. Furthermore, the method of this invention using the cell lines of the invention permits quantitative evaluation of viral particles in the sample, since the parameter measured is the focus of infection, each focus being generated by a single original infectious HIV particle.

Table 2 is provided comparing the prior art cell lines with the cell lines and the techniques of the invention.

TABLE 2

Comparison of human immunodeficiency virus infectivity titers on three different CD-4-positive HeLa cell lines

| Virus | Madden | HIV foci/0.2 ml 6C | 1022 | Rati |
|---|---|---|---|---|
| 13539 | <3 | 57 | 19000 | 3 |
| 13948 | 24 | 48 | 1410 | |
| 13956 | 29 | 512 | 33100 | |
| 14114 | 15 | 100 | 6020 | |
| 208K#2 | 13 | 141 | 30200 | 2 |
| 208K#6 | 38 | 195 | 20000 | 1 |
| 208K#9 | 8 | 214 | 23000 | 1 |
| 208K#10 | <3 | 19 | 4570 | 2 |
| 14345 | 10 | 26 | 3020 | 1 |
| 14558 | 17 | 246 | 16600 | |
| 212#1 | 6 | 126 | 1350 | |
| NL4-3 | 284 | 214 | 692 | |

NL4-3 is a laboratory adapted HIV clone which grows in many human T cell leukemi All other viruses are HIV isolates from AIDS patients which were passaged 1–2 ti human PHA-stimulated lymphocytes and do not grow in human T cell leukenmia lines. patient isolates not adapted to growth in leukemia cell lines, titers in 1022 ce 333.-fold higher than in 6C cells. Titers in Madden cells were lower than 6C ce None of the patients' lymphocytes tested were positive when analyzed directly by FIA prior to in vitro cultivation. Therefore, based on the number of cells tested, these patient cell populations contained less than one FIA-positive cell per million cells. However, in many cases, co-cultivation in vitro for several days in the presence of normal PHA blasts led to amplification of HIV expression to levels detectable by FIA. In most instances, detection by FIA slightly preceded the appearance of reverse transcriptase. However, this kinetic difference was usually small under these assay conditions.

Chesebro et al., *Virology* 84, 222 (1978) have already found that detection of retrovirus-infected cells by infectivity assays is highly dependent on the rate of infectious virus release by individual cells. Cells releasing virus slowly are detected inefficiently, whereas cells releasing virus rapidly are readily detected. This situation appears also to hold true for cells infected with HIV. Previous studies of peripheral blood mononuclear cells from AIDS patients indicated that cells containing HIV gene sequences could be detected by in situ hybridization at a frequency of around 1 per $10^5$ cells in half of the patients. If the rate of virus production per cell were sufficiently high, such a frequency should be easily within the sensitivity of detection of these cells by FIA. The finding that FIA assays of cells taken directly from patients were consistently negative (i.e., less than one positive cell per $10^6$ cells) but became positive after in vitro co-cultivation, suggested that the rate of virus release was very low in patient peripheral blood cells but was elevated during in vitro cultivation. This conclusion agrees with estimates of very low HIV gene copy numbers observed by in situ hybridization of AIDS patient blood cells. Low virus expression is not usually seen in retroviral diseases, however, central nervous system "latent" infection by visna lentivirus is associated with the presence of a very low number of viral genes and low levels of viral protein and infectivity in infected cells. In this disease, the mechanism of regulation of expression is unknown, but low expression is believed to be important in long-term virus persistence in vivo. Interestingly, similar to the results with HIV, low expression of visna virus was reversed when cells were cultured in vitro.

HIV (LAV strain)-infected A3.01 cells were labelled with $^{35}$S-cysteine at 120 microcuries/ml and $2\times10^6$ cells/ml for eight hours at 37° C. in cysteine-free medium with dialyzed fetal calf serum NIH/3T3 cells infected with vaccinia expressing HIV gp160 or vaccinia expressing influenza (HA) (18) at a multiplicity of 10, and twenty hours later cells were labelled with $^{35}$S-methionine at 100 microcuries/ml for two hours at 37° C. in methionine-free medium.

After labelling, the cells were precleared and processed from immunoprecipitation using $9\times10^5$ cell equivalents of lysate of 0.10 ml of NP40-lysed culture supernatant fluid incubated with 1 ml of hybridoma tissue culture supernatant or 3 microliters human AIDS patient serum. Then, 0.1 ml of a 10% suspension of Sepharose® protein A (Pharmacia) was added, incubated for thirty minutes with gentle rocking, and the beads were then washed three times with lysing buffer, eluted and analyzed by SDS-PAGE in 8% polyacrylamide gels followed by fluorography as described by Chesebro et al., *Virology* 112, 131 (1981).

Hybridomas producing monoclonal antibodies specific for HIV envelope proteins were obtained from spleen cells of (BIO.A(2R) X A.BY)F mice immunized with a×$10^7$ PFU of vaccinia virus expressing HIV gp160 (1B) first in a tail scratch and three to five weeks later intraperitoneally. Three days after the second inoculation, spleen cells were fused with NS1 cells.

Supernatant fluids were screened by indirect immunofluorescence on methanol-fixed 8E5 cells which chronically express HIV envelope and gag proteins. Six positive clones were obtained from one mouse, and they appeared to represent at least two distinct clones (antibodies 902 and 907) based on differences in L chain migration in SDS-PAGE gels. All antibodies were of IgG$_1$ subclass, and in lysing buffer, all bound to Sepharose protein A, but not to heat and formalin-fixed staph A (Cowan I strain). All antibodies were specific for HIV gp120 based on reactivity in indirect immunofluorescence with methanol-fixed CV-1 cells infected with vaccinia expressing HIV gp160 or gp120. No reactivity was observed against CV-1 cells infected with vaccinia expressing influenza HA. Furthermore, these antibodies reacted in indirect immunofluorescence with live and methanol-fixed A3.01 cells and MOLT-4 cells infected with HIV (LAV strain), H9 cells infected with HIV (HTLV IIIB strain), and 8E5 cells, but were nonreactive with uninfected A3.01, MOLT4, and H9 cells, or with A3.01 cells or PHA blast cells infected with all other HIV isolates tested so far.

Figure 1A:
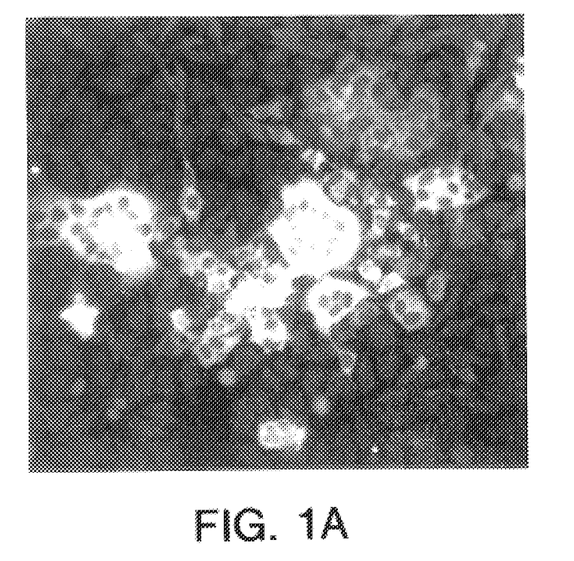
FIG. 1 shows foci of a variety of infected HIV(LAV strain)-infected HT4-6C cells.

FIG. 1A shows the foci of HAV (LAV strain)-infected HT4-6C cells detected by indirect immunofluorescence using monoclonal antibody 902, specific for HIV gp120. The field shown has a single focus of HIV-infected cells including some multinucleated giant cells and some mononuclear cells.

Figure 1B:
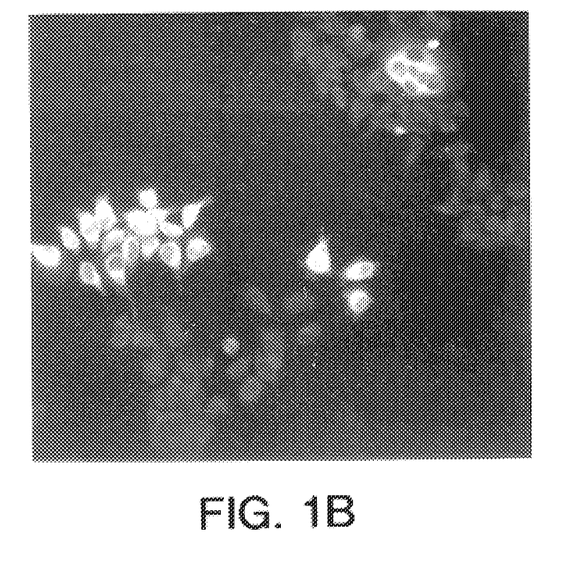

FIG. 1B shows the foci of HIV (LAV)-infected HT4-6C cells showing one area of HIV-positive mononuclear cells and one giant cell with six nuclei.

Figure 1C:
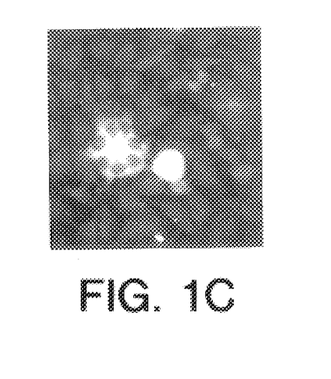
Figure 1D:
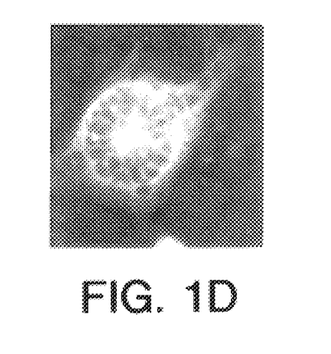

FIGS. 1C and 2D show foci of HIV (5888 patient isolate) infected HT4-6C cells detected by human AIDS patient serum and FITC-anti-human Ig. Both foci consist of a single multinucleated giant cell expressing HIV antigens. With wild-type HIV isolates, only rarely have mononuclear HT4-6C cells expressing HIV been observed.

Figure 1E:
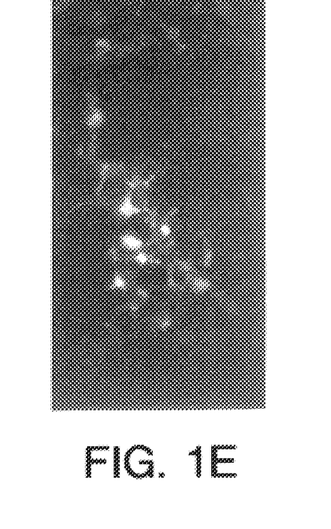

FIG. 1E shows the focus of HIV(LAV)-infected HT4-6C cells detected using the FIA on a live cell monolayer. It should be noted that the multinucleated cells are not visible and appear to have been removed during the multiple washes of the FIA procedure.

The details of the focal immunoassay performed for these figures are as follows: $5 \times 10^4$ HT4-6c cells were seeded in 35 mm plastic tissue culture wells with 2.5 ml, RPMI 1640 plus 10% fetal calf serum. The following day, various numbers of HIV-infected A3.01 or PHA blast cells were added to the wells. Eighteen hours later, the suspended cells were removed, and HT4-6C cells were fed and allowed to grow for three more days. The medium was then removed, the attached cells were fixed five minutes with methanol, rinsed with PBS, and processed for indirect immunofluorescence. The wells were incubated for twenty minutes at room temperature with either 0.15 ml of hybridoma tissue culture fluid (antibody 902) or 0.15 ml of a 1/300 dilution of human AIDS patient serum selected for low background against uninfected HT4-6C cells. The cells were then rinsed with 2 ml PBS, incubated for thirty minutes with 0.15 ml of a 1/180 dilution of FITC-conjugated goat or rabbit antibodies specific for either mouse or human immunoglobulins, rinsed again with PBS, and either examined immediately in an inverted fluorescence microscope as previously described by Sitbon et al., *Virology* 141, 110 (1985), or refluxed for five minutes with methanol and stored in PBS with 0.002 M EDTA at 4°/C. for future examination. FIA on live infected cells was identical except that the original fixation with methanol was omitted.

Figure 2:
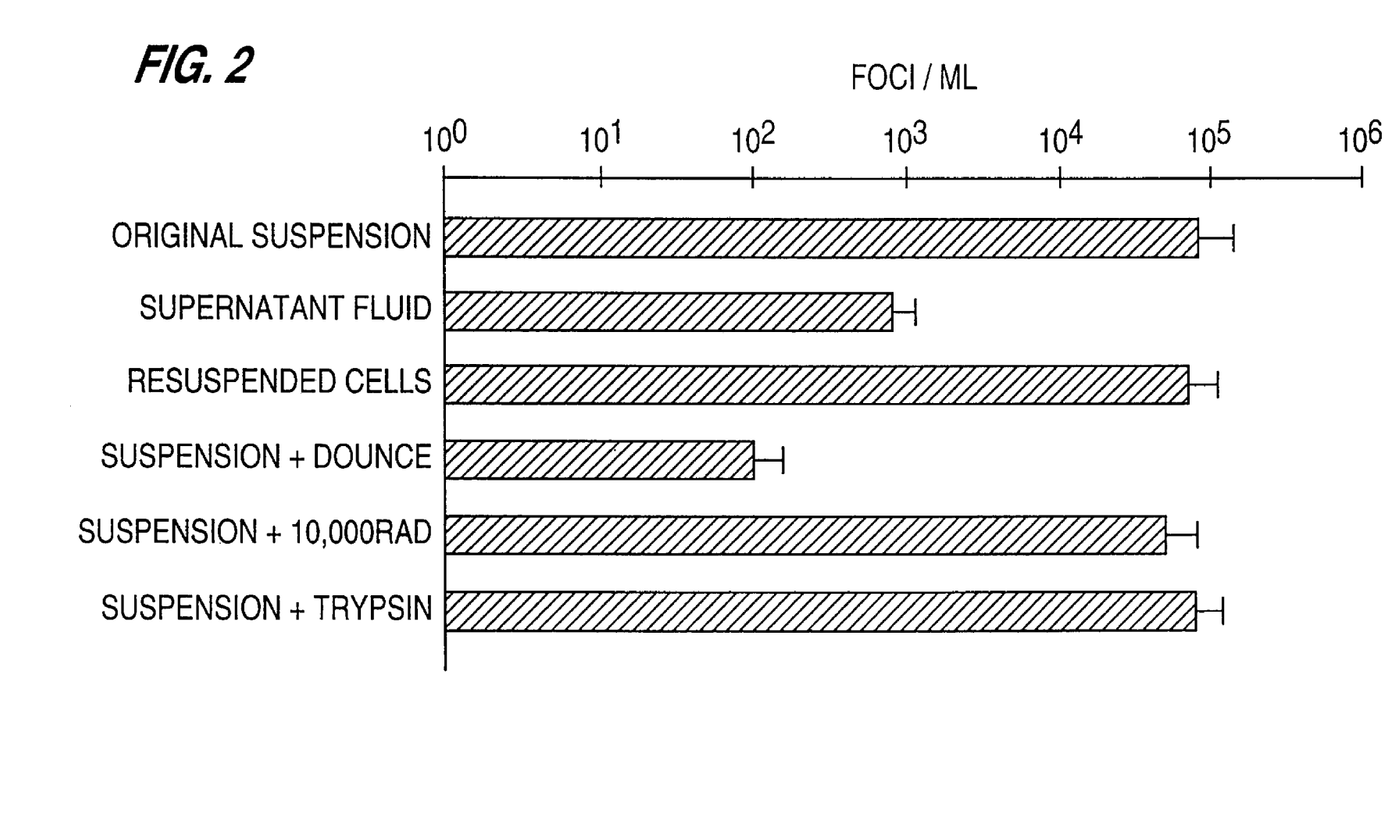
FIG. 2 shows the foci of HIV-infection in HT4-6C cells.

In FIG. 2, the foci of HIV infection in HT4-6C cells were detected by FIA four days after infection with HIV-infected A3.01 cells after various treatments. Data shown were obtained using monoclonal 902 as the first antibody, but similar results were obtained with human anti-HIV serum followed by FITC-conjugated rabbit anti-human immunoglobulin. A3.01 suspension cultures were used six days after infection with a 1/10 dilution of HIV (LAV strain). Infected cells were seeded directly, or were washed twice by centrifugation, resuspended at their original concentration ($3 \times 10^5$ cells/ml), and then treated with: 10,000 rad X-irradiation to prevent subsequent cell division, digestion for ten minutes with 0.02% trypsin in 2 mM EDTA with 0.15 ml NaCl to inactivate extracellular virus, or lysed by Dounce homogenization to kill cells directly. These samples as well as untreated control cells were then placed in HT4-6C cultures for analysis by FIA.

Figure 3A:
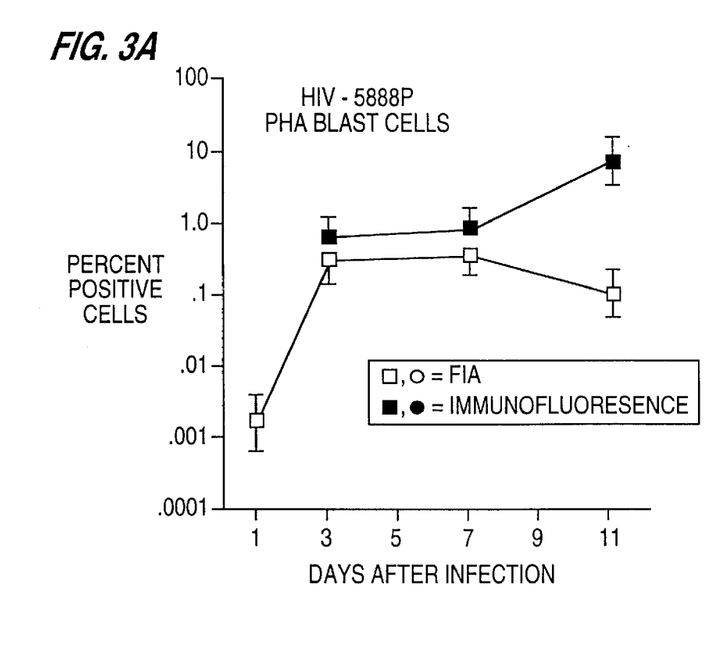
FIG. 3 shows the correlation of HIV-infected lymphoid cells detected by FIA and by indirect immunofluorescence at various times after infection.
Figure 3B:
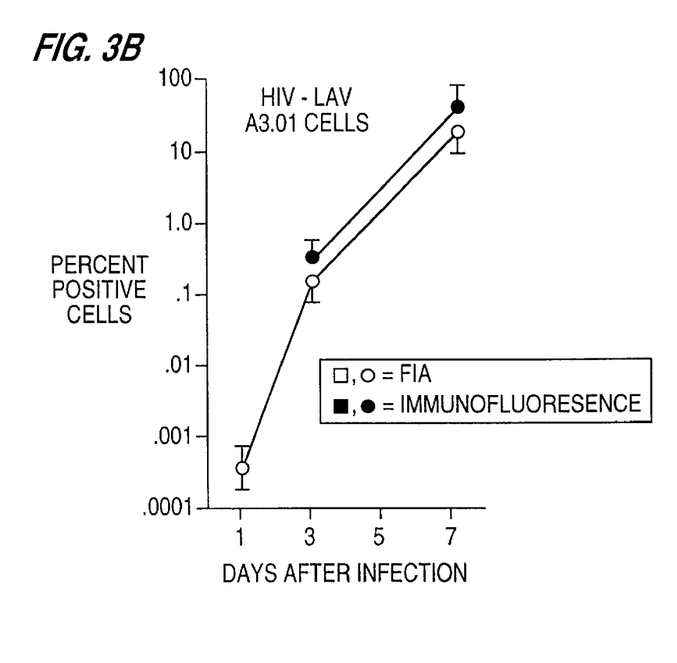

FIGS. 3A and 3B show the correlation of HIV-infected lymphoid cells detected by FIA and by indirect immunofluorescence at various times after infection. Lymphocytes blast cells were infected with an AIDS patient HIV isolate (5888P) three days after PHA stimulation. A3.01 cells were infected with HIV (LAV strain). Infected cells were cultured in vitro and assayed at various days by FIA on HT4-6C cells or by indirect immunofluorescence on methanol-fixed lymphoid cells using monoclonal antibody 902 and FITC-conjugated anti-mouse Ig for HIV LAV and human AIDS patient serum plus FITC-conjugated anti-human Ig for HIV-5888P.

Figure 4:
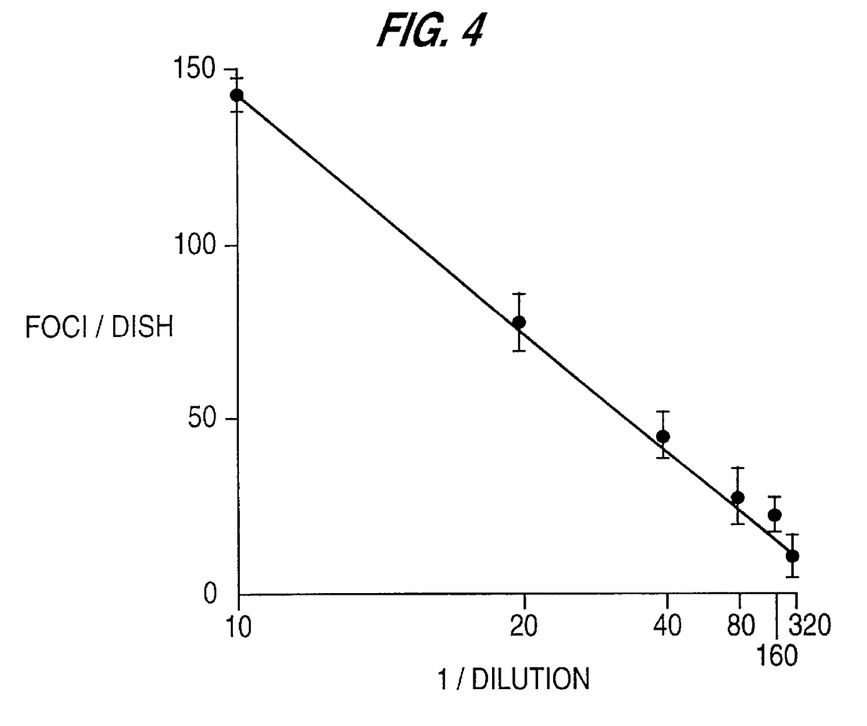
FIG. 4 shows FIA of HIV (LAV strain) from infected A3.01 cell cultures used to infect HT4-6C cell monolayers.

In FIG. 4, HIV (LAV strain) from infected A3.01 cell cultures was used to infect HT4-6C cell monolayer. Infection was accomplished adding 0.5 ml of the dilutions shown to 3 ml culture medium without polybrene or DEAE-dextran. Twenty four hours later the medium was changed, and FIA was done on the fourth day after infection.

EXAMPLE I

The effects of drug therapy are monitored in patients suffering from AIDS by taking serum samples from the patients and testing for the presence of HIV-infected cells according to the above-described procedure. A decrease in the number of HIV-infected cells during the course of therapy is a positive indication of the efficacy of the drug against the disease.

EXAMPLE II

HIV expression can be quantified in asymptomatic HIV antibody-positive patients by testing for the presence of HIV in the serum of these patients according to the procedure of the present invention.

EXAMPLE III

The virus neutralizing antibody in serum is measured using the assay procedure as described above.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

Undoubtedly the present invention for determining presence HIV virus grows more important as more anti-AIDS drugs become available and as tests for viral resistance to the drug which is being used on a particular patient become desirable. By the method of the invention, HIV-susceptible cells are attached to a solid substrate and exposed to the test material to be investigated for presence of HIV virus. The assay as method for detecting drug-resistant HIV strains in those undergoing treatment for HIV infection will become increasingly important as more therapeutic options are available to the practitioner. (See Larder, et al, "HIV with Reduced Sensitivity to Zidovidine (AZT) Isolated During Prolonged Therapy" *Science, Vol.* 243, pp1731–1734.) The method provides a means if determining the number of infectious HIV particles in a sample by counting the foci of HIV-positive cells in a field. HIV positive cells are detected by the presence of HIV proteins or nucleic acids in individual cells using appropriate antibodies or probes, or by the typical HIV-induced changes in cell morphology such as fusion and syncytia formation. The progress of the disease as measured by the number of HIV virus in a sample.

For detecting inhibitor drug-resistant HIV strains, the cells are infected with HIV and incubated for 3 days in the presence of different drug concentration. The HIV foci are then counted. The concentration of drug required to reduce the number of foci by 50% or 95% is then calculated. Because the method provides a means of identifying foci, the method is quantitative, and can be used as a method to evaluate sensitivity of a particular patient's viral strain to various therapeutic agents. Hence, it provides a means for the physician to choose the particular anti-AIDS drug which is most likely to be effective for inhibiting the strain of HIV infecting an individual.

The techniques could also be used to screen new drugs of efficacy against HIV.

The cell lines HT4-6C (ATCC accession No. CRL-9631) and 1022 (ATCC accession No. CRL-10284) have been deposited in the American Type Culture Collection in Rockville, Md. under the provisions of the Budapest Treaty. The deposit will be maintained in accord with that treaty. After the patent is granted, the deposited cell line will be accessible to the public.

The deposit will be stored with care necessary to keep it viable and uncontaminated for a period of at least five years after the most recent request for furnishing a sample of the cell line and, in any case, at least thirty (30) years after the date of the deposit or for the enforceable life of the patent, whichever is longer.

We claim:

1. A HeLa cell line having the properties of adherence to plastic surfaces, of growth in a monolayer, and of susceptibility to infection by human immunodeficiency virus of cell line HT4-6C.

2. A HeLa cell line having all of the identifying characteristics of cell line HT4-6C, accession number ATCC CRL-963 1.

3. A HeLa cell line having the properties of adherence to plastic surfaces, of growth in a monolayer, and of susceptibility to infection by human immunodeficiency virus of cell line 1022.

4. A HeLa cell line having all of the identifying characteristics of cell line 1022, accession number ATCC CRL-10284.

5. HeLa cell line HT4-6C, ATCC accession number CRL-963 1.

6. HeLa cell line 1022, ATCC accession number CRL-10284.

7. A combination comprising a surface having attached thereto a smooth monolayer of cells of HeLa cell line HT4-6C.

8. A combination comprising a surface having attached thereto a smooth monolayer of cells of HeLa cell line 1022.

* * * * *